United States Patent
Peultier et al.

(10) Patent No.: US 8,246,623 B2
(45) Date of Patent: Aug. 21, 2012

(54) PROGRESSIVE REDUCTION INSTRUMENT FOR REDUCTION OF A VERTEBRAL ROD AND METHOD OF USE

(75) Inventors: Bertrand Peultier, Les Hopitaux Neufs (FR); Sean Molloy, Buckinghamshirre (GB)

(73) Assignee: Warsaw Orthopedic, Warsaw, IN (US)

( * ) Notice: Subject to any disclaimer, the term of this patent is extended or adjusted under 35 U.S.C. 154(b) by 276 days.

(21) Appl. No.: 12/358,416

(22) Filed: Jan. 23, 2009

(65) Prior Publication Data
US 2010/0121386 A1 May 13, 2010

(30) Foreign Application Priority Data
Nov. 13, 2008 (FR) .................................. 08 57514

(51) Int. Cl.
*A61B 17/70* (2006.01)
(52) U.S. Cl. ...................... 606/86 A; 606/246
(58) Field of Classification Search .......... 606/246–279, 606/86 A, 914, 916
See application file for complete search history.

(56) References Cited

U.S. PATENT DOCUMENTS

| | | | |
|---|---|---|---|
| 4,409,968 A | 10/1983 | Drummond | |
| 4,411,259 A | 10/1983 | Drummond | |
| 4,877,020 A | 10/1989 | Vich | |
| 4,963,144 A | 10/1990 | Huene | |
| 5,020,519 A | 6/1991 | Hayes et al. | |
| 5,041,028 A * | 8/1991 | Stohle | 439/822 |
| 5,281,223 A | 1/1994 | Ray | |
| D346,217 S | 4/1994 | Spaker et al. | |
| 5,334,205 A | 8/1994 | Cain | |
| 5,364,397 A | 11/1994 | Haynes et al. | |
| 5,616,143 A | 4/1997 | Schlapfer et al. | |
| 5,720,751 A | 2/1998 | Jackson | |
| 5,910,141 A | 6/1999 | Morrison et al. | |
| 5,941,885 A | 8/1999 | Jackson | |
| 6,123,707 A | 9/2000 | Wagner | |
| 6,183,472 B1 | 2/2001 | Lutz | |
| 6,251,111 B1 | 6/2001 | Barker et al. | |
| 6,379,356 B1 | 4/2002 | Jackson | |
| 6,648,888 B1 | 11/2003 | Shluzas | |
| 6,660,006 B2 | 12/2003 | Markworth et al. | |
| 6,726,692 B2 | 4/2004 | Bette | |
| 6,730,089 B2 | 5/2004 | Jackson | |

(Continued)

FOREIGN PATENT DOCUMENTS
WO 2009152302 12/2009
(Continued)

OTHER PUBLICATIONS
INPI, Preliminary Search Report, Jun. 5, 2009.
(Continued)

*Primary Examiner* — Eduardo C Robert
*Assistant Examiner* — Nicholas Plionis

(57) ABSTRACT

An instrument and method for reducing a vertebral rod into an anchor attached to a vertebral member. The instrument may include a gripper and an attached reduction member that includes a handle and shaft. The gripper is configured to attach to an anchor and may include an asymmetrical shape to accommodate the anatomy of a patient and a funneled capturing space to facilitate reduction of the vertebral rod. The reduction member may be configured to apply a reduction force to the vertebral rod at the various axial and lateral medial positions within the capturing space. The reduction member may also provide for course and fine movement of the shaft during the movement of the vertebral rod.

13 Claims, 12 Drawing Sheets

U.S. PATENT DOCUMENTS

| | | |
|---|---|---|
| 6,743,231 B1 | 6/2004 | Gray et al. |
| 6,746,449 B2 | 6/2004 | Jones et al. |
| 6,790,208 B2 | 9/2004 | Oribe et al. |
| 7,090,679 B2 | 8/2006 | Saint-Martin et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,278,995 B2 | 10/2007 | Nichols et al. |
| 7,341,594 B2 | 3/2008 | Shluzas et al. |
| 7,371,239 B2 | 5/2008 | Dec et al. |
| 7,461,574 B2 | 12/2008 | Lewis et al. |
| 7,470,279 B2 | 12/2008 | Jackson |
| 7,491,207 B2 | 2/2009 | Keyer et al. |
| 7,572,281 B2 | 8/2009 | Runco et al. |
| 7,575,581 B2 | 8/2009 | Lovell |
| 7,608,081 B2 | 10/2009 | Abdelgany |
| 7,618,440 B2 | 11/2009 | Gray et al. |
| 7,618,444 B2 | 11/2009 | Shluzas |
| 7,621,918 B2 | 11/2009 | Jackson |
| 7,651,502 B2 | 1/2010 | Jackson |
| 7,666,189 B2 | 2/2010 | Gerber et al. |
| 7,713,274 B2 | 5/2010 | Shluzas et al. |
| 7,758,617 B2 | 7/2010 | Lott et al. |
| 7,771,430 B2 | 8/2010 | Jones et al. |
| 7,776,040 B2 | 8/2010 | Markworth et al. |
| 7,815,650 B2 | 10/2010 | Shluzas et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 2003/0225408 A1 | 12/2003 | Nichols et al. |
| 2004/0034350 A1 | 2/2004 | St. Onge et al. |
| 2004/0147936 A1 | 7/2004 | Rosenberg et al. |
| 2004/0147937 A1 | 7/2004 | Dunbar, Jr. et al. |
| 2004/0249378 A1 | 12/2004 | Saint Martin et al. |
| 2004/0267275 A1 | 12/2004 | Cournoyer et al. |
| 2005/0033299 A1 | 2/2005 | Shluzas |
| 2005/0149036 A1 | 7/2005 | Varieur et al. |
| 2005/0149053 A1 | 7/2005 | Varieur et al. |
| 2005/0261702 A1 | 11/2005 | Oribe et al. |
| 2006/0009775 A1 | 1/2006 | Dec et al. |
| 2006/0069391 A1 | 3/2006 | Jackson |
| 2006/0079909 A1 | 4/2006 | Runco et al. |
| 2006/0089651 A1 * | 4/2006 | Trudeau et al. ................ 606/86 |
| 2006/0111712 A1 | 5/2006 | Jackson |
| 2006/0111730 A1 | 5/2006 | Hay |
| 2006/0149291 A1 | 7/2006 | Selover |
| 2006/0217735 A1 | 9/2006 | MacDonald et al. |
| 2006/0247630 A1 | 11/2006 | Lott et al. |
| 2007/0032162 A1 | 2/2007 | Jackson |
| 2007/0043378 A1 | 2/2007 | Kumar et al. |
| 2007/0078460 A1 | 4/2007 | Figg et al. |
| 2007/0093849 A1 | 4/2007 | Jones et al. |
| 2007/0213722 A1 | 9/2007 | Jones et al. |
| 2007/0233079 A1 | 10/2007 | Fallin et al. |
| 2007/0260261 A1 | 11/2007 | Runco |
| 2007/0270867 A1 | 11/2007 | Miller et al. |
| 2007/0270869 A1 | 11/2007 | Young et al. |
| 2007/0276379 A1 | 11/2007 | Miller et al. |
| 2007/0282337 A1 | 12/2007 | Garamszegi |
| 2008/0004629 A1 | 1/2008 | Nichols et al. |
| 2008/0009864 A1 | 1/2008 | Forton et al. |
| 2008/0015601 A1 | 1/2008 | Castro et al. |
| 2008/0051794 A1 | 2/2008 | Dec et al. |
| 2008/0091213 A1 | 4/2008 | Jackson |
| 2008/0154277 A1 | 6/2008 | Machalk |
| 2008/0195155 A1 | 8/2008 | Hoffman et al. |
| 2008/0221626 A1 | 9/2008 | Butters et al. |
| 2008/0228233 A1 | 9/2008 | Hoffman et al. |
| 2008/0234678 A1 | 9/2008 | Gutierrez et al. |
| 2008/0234765 A1 | 9/2008 | Frasier et al. |
| 2008/0243190 A1 | 10/2008 | Dziedzic et al. |
| 2008/0288005 A1 | 11/2008 | Jackson |
| 2009/0018593 A1 | 1/2009 | Barrus et al. |
| 2009/0030419 A1 * | 1/2009 | Runco et al. ................ 606/99 |
| 2009/0082775 A1 | 3/2009 | Altarac et al. |
| 2009/0088764 A1 | 4/2009 | Stad et al. |
| 2009/0105712 A1 | 4/2009 | Dauster et al. |
| 2009/0157125 A1 | 6/2009 | Hoffman et al. |
| 2009/0171391 A1 | 7/2009 | Hutton et al. |
| 2009/0228053 A1 | 9/2009 | Kolb et al. |
| 2009/0228055 A1 | 9/2009 | Jackson |
| 2009/0228056 A1 | 9/2009 | Jackson |
| 2009/0281582 A1 | 11/2009 | Villa et al. |
| 2009/0318972 A1 | 12/2009 | Jackson |
| 2009/0318975 A1 | 12/2009 | Abdelgany |
| 2010/0004696 A1 | 1/2010 | Jackson |
| 2010/0024487 A1 | 2/2010 | Khoo et al. |
| 2010/0036434 A1 | 2/2010 | Ely |
| 2010/0036443 A1 | 2/2010 | Hutton et al. |
| 2010/0121385 A1 | 5/2010 | Blain et al. |
| 2010/0137875 A1 | 6/2010 | Marino et al. |
| 2010/0185242 A1 | 7/2010 | Barry et al. |
| 2010/0185248 A1 | 7/2010 | Barry et al. |
| 2010/0228302 A1 | 9/2010 | Dauster et al. |
| 2010/0249856 A1 | 9/2010 | Lott et al. |
| 2010/0274252 A1 | 10/2010 | Bottomley et al. |
| 2010/0292742 A1 | 11/2010 | Stad et al. |

FOREIGN PATENT DOCUMENTS

| | | |
|---|---|---|
| WO | 2009152308 | 12/2009 |

OTHER PUBLICATIONS

International Searching Authority, ISR and Written Opinion, Jul. 27, 2010.

* cited by examiner

PROGRESSIVE REDUCTION INSTRUMENT FOR REDUCTION OF A VERTEBRAL ROD AND METHOD OF USE

BACKGROUND

The present application is directed to instruments and methods for moving a vertebral rod within a patient and into a bone anchor attached to a vertebral member and, more particularly, to instruments with an asymmetrical shape to facilitate insertion into the patient and movement of the vertebral rod into the bone anchor.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Elongated members may be attached to the vertebral members to various reasons such as to provide support, redirect stresses over a wider area away from a damaged or defective region, and restore the spine to its proper alignment. The elongated members are secured to one or more vertebral members through connectors. The connectors include a receiver that receives the elongated member, and an anchor to anchor into the vertebral member.

Instruments are needed to insert or reduce the elongated members into the anchors. The instruments should be sized and shape for insertion into the patient and connection to the bone anchors. The instruments should be designed for effective and efficient movement of the vertebral rod into the anchor.

SUMMARY

The present application discloses instruments and methods for moving a vertebral rod into a bone anchor that is attached to a vertebral member. The instrument may include a gripper with opposing first and second arms. The arms may include distal ends that may be configured to attach to the bone anchor. A capturing space is formed between inner sides of the arms to receive the vertebral rod. The capturing space may include an asymmetrical shape with a funneled width that reduces from an enlarged width at a proximal end and a reduced width at a distal end. The instrument may also include a reduction member that may include a handle and a shaft. The reduction member attaches to the vertebral rod and is configured to move the vertebral rod along the capturing space and into the anchor. Once the vertebral rod is within the anchor, the instrument may be detached from the anchor and from the patient.

The various aspects of the various embodiments may be used alone or in any combination, as is desired.

DETAILED DESCRIPTION

Figure 1:
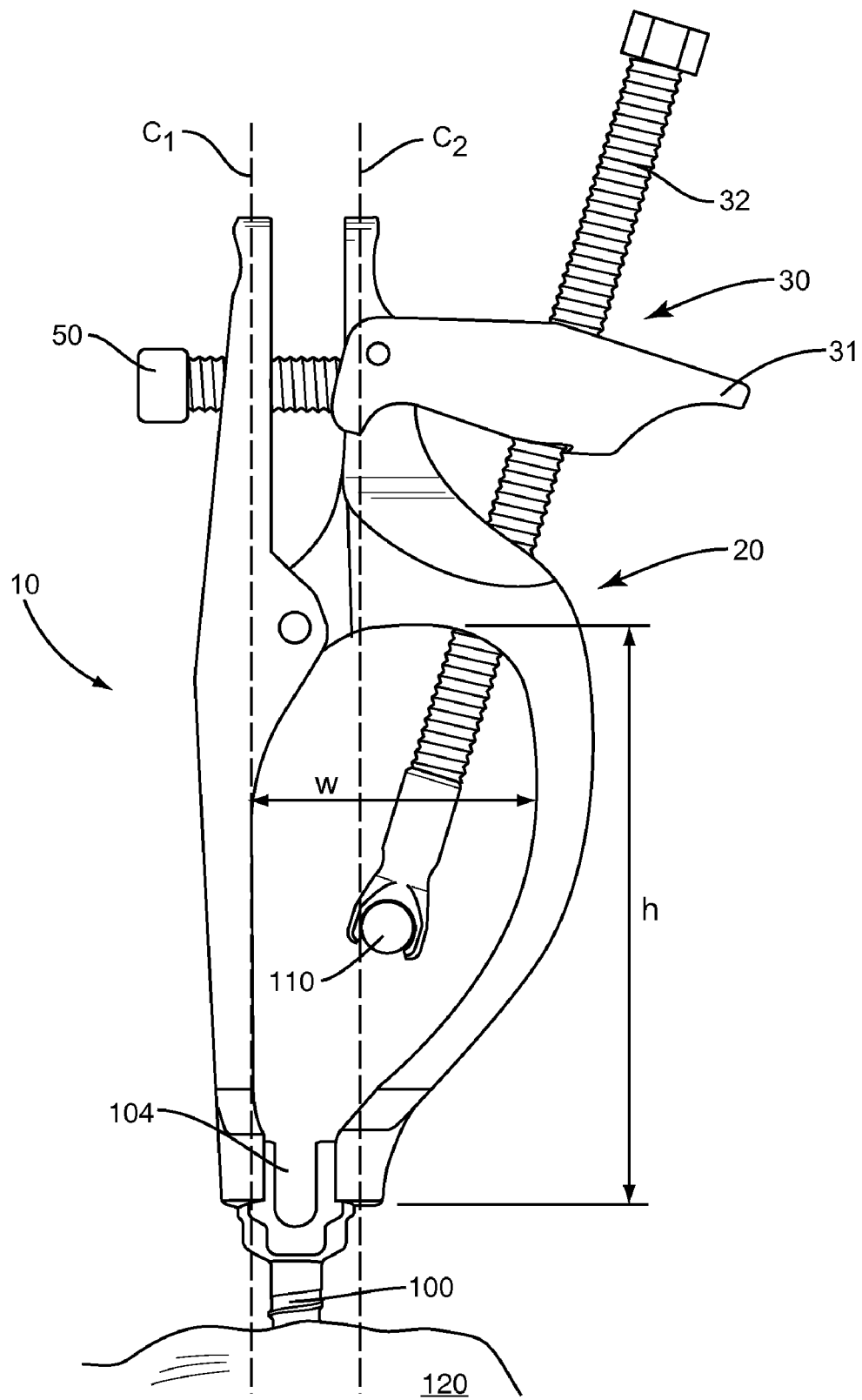
FIG. 1 is a side view of a reduction instrument according to one embodiment.

The present application is directed to instruments and methods for reduction of a vertebral rod into an anchor attached to vertebral members. FIG. 1 includes an embodiment of the instrument 10 that generally includes a gripper 20 and a reduction member 30 including a handle 31 and shaft 32. The gripper 20 is configured to attach to an anchor 100 and may include an external asymmetrical shape to accommodate the anatomy of the patient and an asymmetrical funneled capturing space 61 to facilitate reduction of the vertebral rod 110 in an axial direction along the gripper 20 from a proximal section to the distal end. The reduction member 30 is configured to apply a reduction force to the vertebral rod 110 in the various axial and lateral positions within the capturing space 61. The reduction member 30 may also provide for course and fine movement of the shaft 32 during the reduction of the vertebral rod 110.

Figure 2:
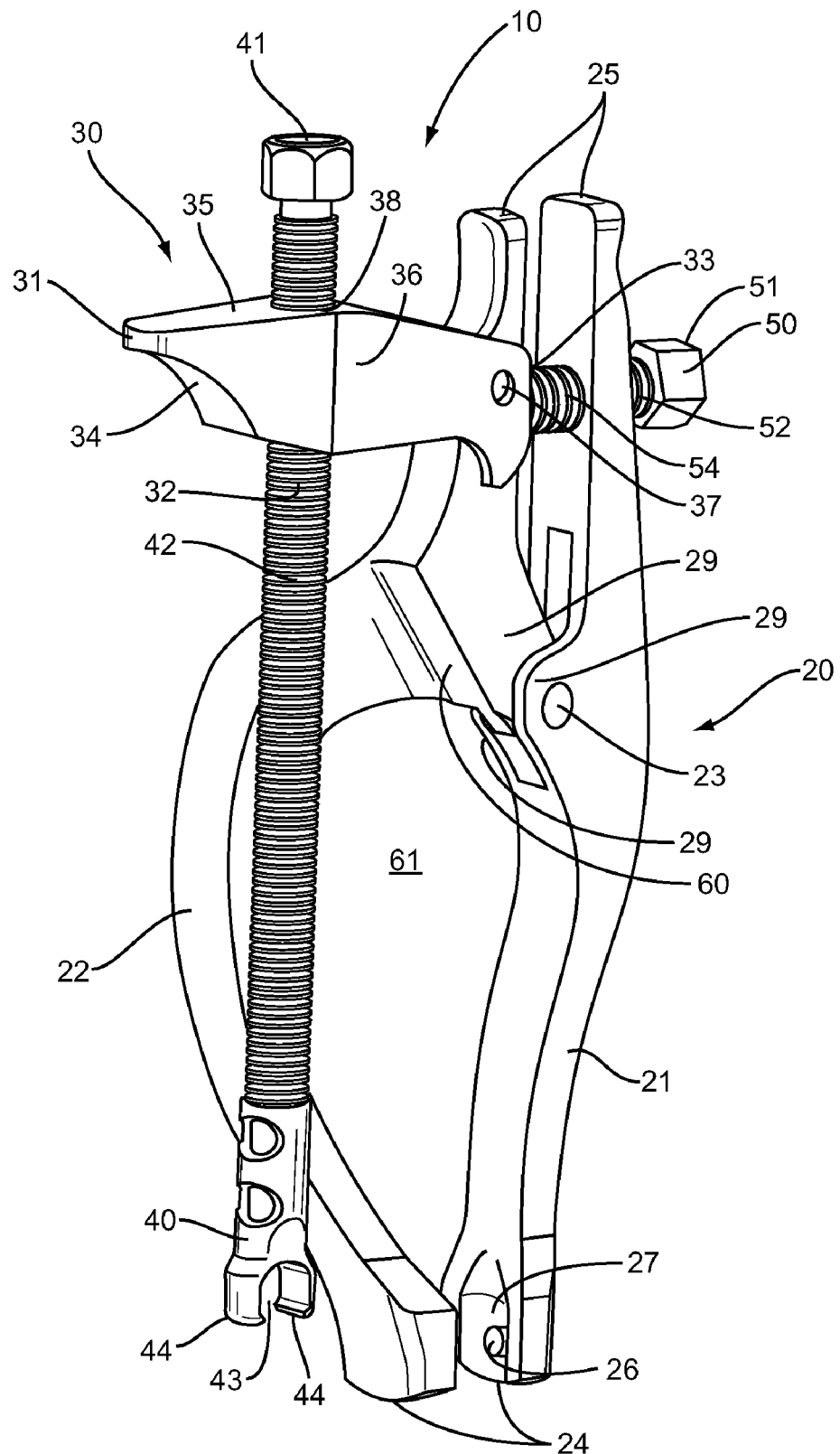
FIG. 2 is a perspective view of a reduction instrument according to one embodiment.

The gripper 20 attaches to the anchor 100 as illustrated in FIGS. 1 and 2. The gripper 20 includes a first jaw 21 and a second jaw 22 that each includes a distal end 24 that attaches to the anchor 100, and a proximal end 25. The jaws 21, 22 are attached together at a pivot 23 positioned between the distal and proximal ends 24, 25 and may include a pin, rivet, or other like mechanical piece.

The gripper 20 includes an external asymmetrical shape to facilitate insertion into the patient. This asymmetrical shape facilitates insertion of the gripper 20 between the lateral tissues and the medial spinous process to attach to the anchor 100 that may be at various angular positions. The first jaw 21 is substantially straight with a line C1 through the distal and proximal ends 24, 25 extending through a majority of the first jaw 21. The second jaw 22 includes a curved shape with a line C2 through the distal and proximal ends 24, 25 being spaced away from a majority of the second jaw 22. The curved shape of the second jaw 22 may be limited to a distal section between the pivot 23 and the distal end 24. A proximal section of the second jaw 22 between the pivot 23 and proximal end 25 may be substantially straight and extend along the line C2.

Figure 3:
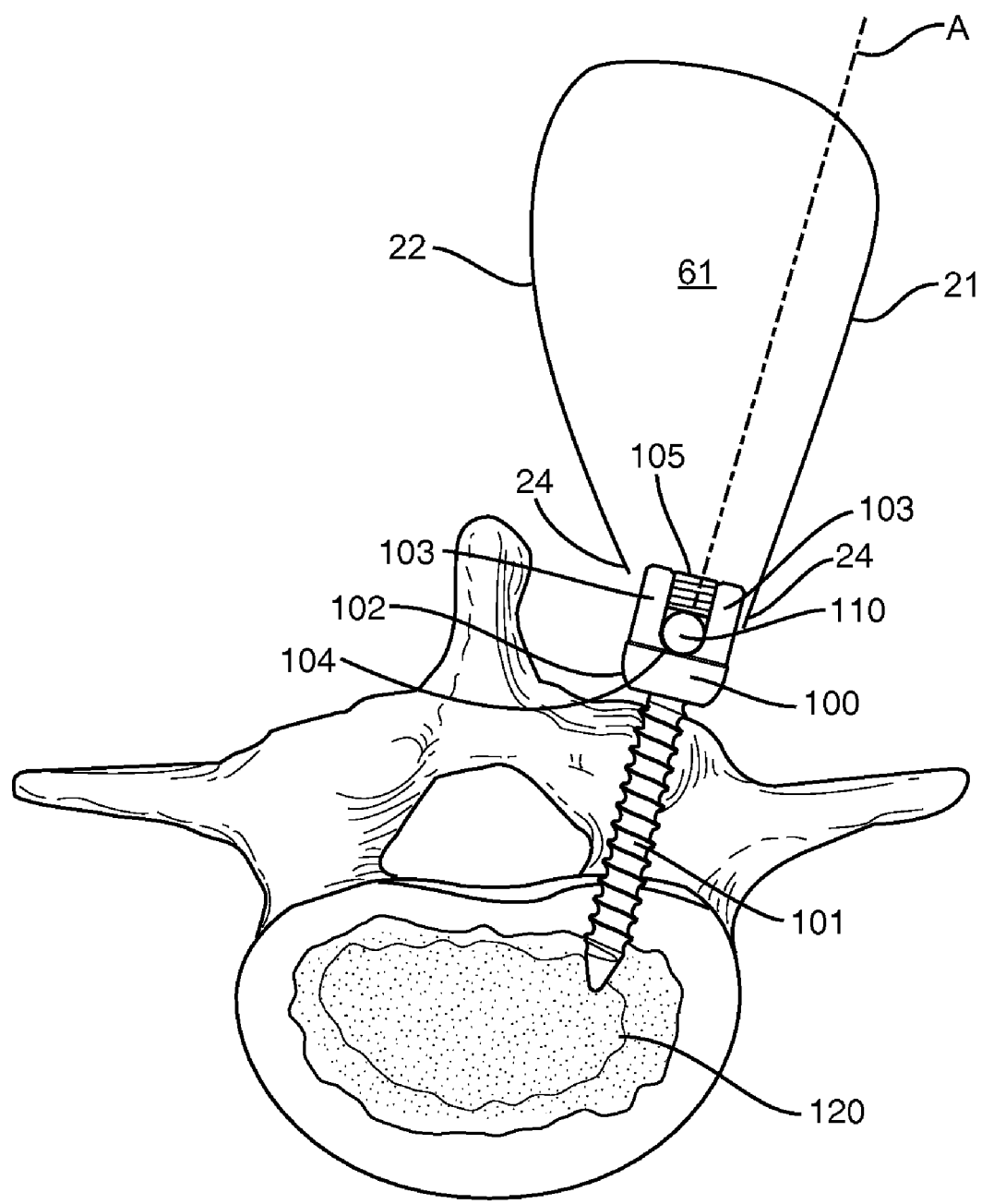
FIG. 3 is a schematic view of a shape of the gripper positioned relative to a vertebral member according to one embodiment.

The shape of the jaws 21, 22 facilitates positioning of the gripper 20 within a patient with the distal ends 24 attached to the anchor 100. FIG. 3 includes a schematic view of the shape of the jaws 21, 22 while attached to the anchor 100. The asymmetrical shape of the jaws 21, 22 takes benefit of the medial-lateral space available within the anatomy of a patient with the anchor 100 attached to the pedicle of the vertebral member 120. The shape provides for the distal ends 24 to attach to the anchor 100 without the jaws 21, 22 interfering with the lateral tissue. The shape also positions a longitudinal axis A that extends through the longitudinal axis of the anchor 100 between the jaws 21, 22. Axis A should be free for access with the fastener 105 and driver tool. Often times it is difficult to insert the fastener 105 because of surrounding tissue and the difficulty in visualizing the axis A. The gripper 20 forms a guide for inserting the fastener 105 driver tool in a manner that is aligned with axis A.

A capturing space 61 is formed between inner sides of the jaws 21, 22. The vertebral rod 110 is captured in the capturing space 61 during the procedure and prevented from escaping by the jaws 21, 22. The space 61 includes a funnel shape with a greater width measured between the inner sides of the jaws 21, 22 at a proximal end that decreases to a minimum width at a distal end. The funnel shape facilitates axial reduction of the vertebral rod 110 in a distal direction along the gripper 20 and into the anchor 100. In one embodiment, a width w of the capturing space 61 is about 25 mm and a height h is about 60 mm. The inner sides of the jaws 21, 22 may be smooth to facilitate movement of the vertebral rod 110 along the surfaces during the reduction.

Figure 4A:
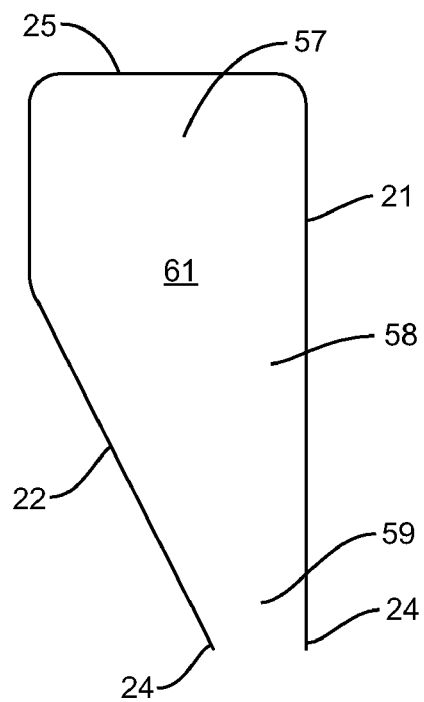
FIG. 4A is a schematic view of a capturing space according to one embodiment.
Figure 4B:
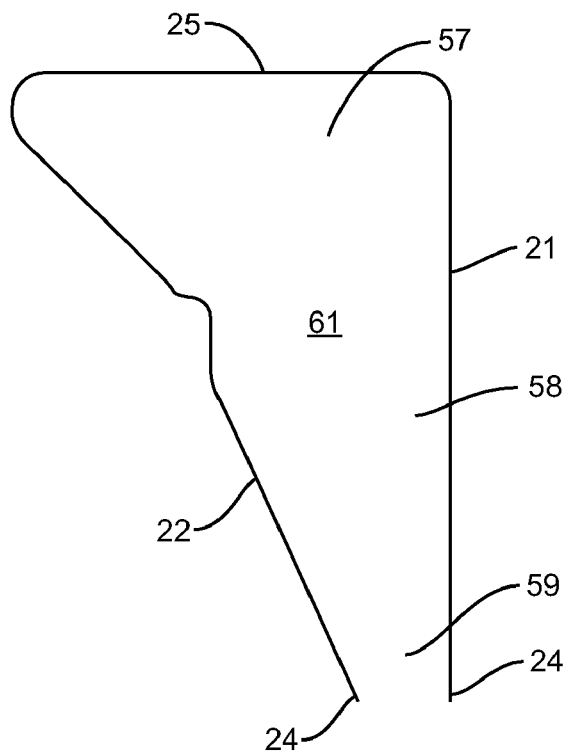
FIG. 4B is a schematic view of a capturing space according to one embodiment.

The capturing space 61 is funneled to facilitate the movement of the vertebral rod 110 axially along the gripper 20 and into the bone anchor 100. The funneled shape may be continuous with the width continuously decreasing from the proximal section to the distal section. The funneled shape may also include non-tapering sections. FIG. 4A includes a shape with the proximal section 57 including a substantially constant width with an intermediate section 58 and distal section 59 being tapered. FIG. 4B includes a shape with the intermediate section 58 including a substantially constant width and the proximal and distal sections 57, 59 being tapered.

One or both jaws 21, 22 of the gripper 20 may also include extensions 29 as illustrated in FIG. 2. The extensions 29 extend outward from a main section of the jaws 21, 22 and may be placed in an overlapping arrangement to position the pivot 23. In one embodiment, one jaw 21, 22 includes a pair of spaced-apart extensions 29 that are sized to extend on each side of the extension 29 on the opposing jaw 21, 22.

Figure 5:
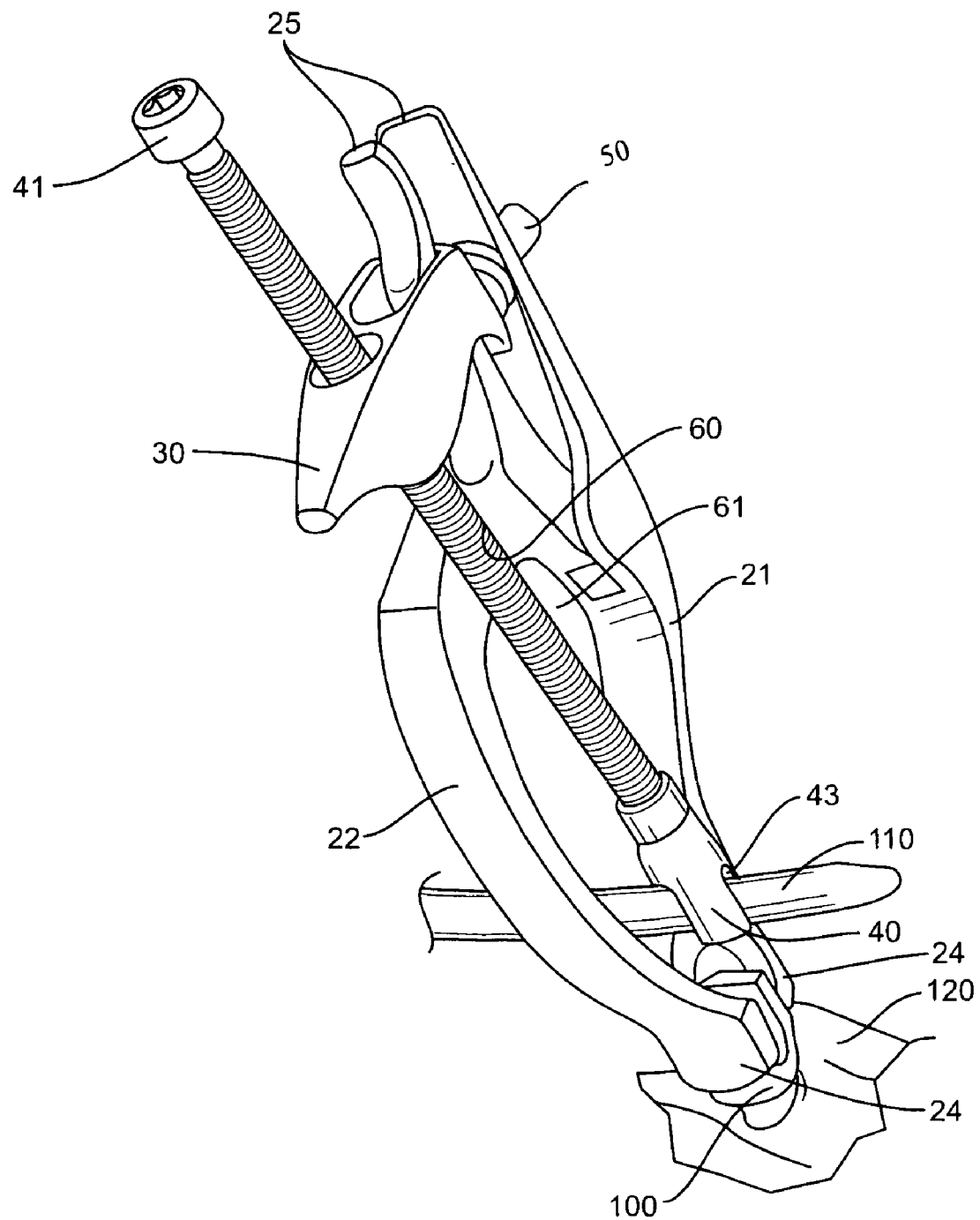
FIG. 5 is a perspective view of a reduction instrument attached to an anchor according to one embodiment.

The second jaw 22 may also be configured to accommodate the shaft 32 of the reduction member 30. Second jaw 22 may include a curved shape that bows out of a plane that extends through the distal and proximal ends 24, 25 as best illustrated in FIG. 5. The amount of bow is adequate for positioning the shaft 32 and still keeping a small profile that allows for an instrument 10 to be attached to the adjacent anchors 100 that extend along the spine. The curved shape may be limited to the distal section of the second jaw 22 between the pivot 23 and the distal end 24. The proximal section may be substantially straight and be aligned along the plane that extends through the distal and proximal ends 24, 25. The second jaw 22 may also include a notch 60 to accommodate the shaft 32. The notch 60 includes a surface that faces towards the shaft 32. The width of the notch 60 may be greater than the width of the shaft 32.

Figure 6:
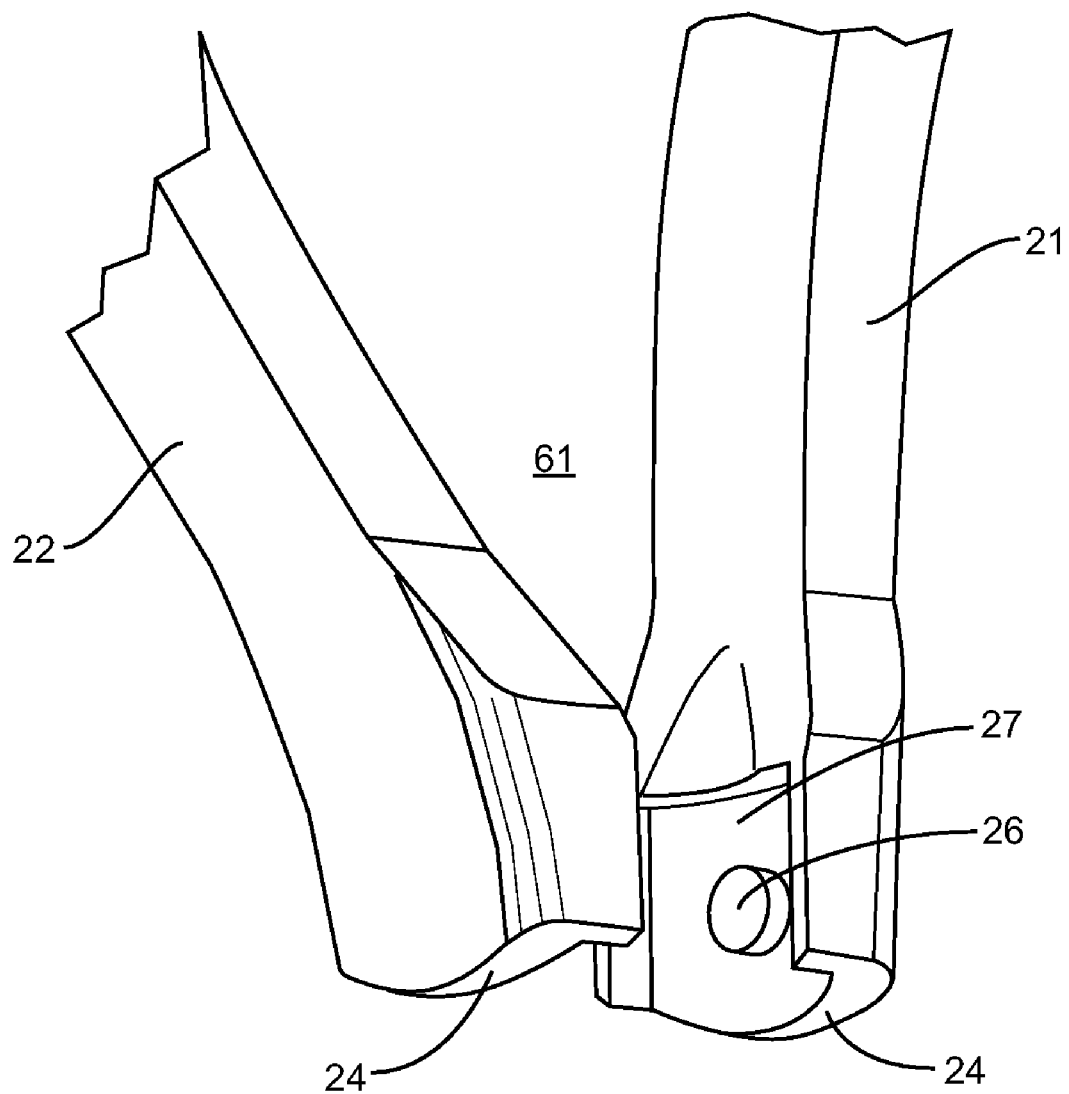
FIG. 6 is a perspective view of the distal ends of a gripper according to one embodiment.

As illustrated in FIG. 6, the distal ends 24 may include scallops 27 on the inner surfaces that are sized to receive the anchor 100. The scallops 27 may extend inward from the distal ends 24 various distances to accommodate the anchors 100. The edges opposite from the distal ends 24 may be linear to match the top surface of the anchor head 101. Tabs 26 may extend outward from one or both scallops 27 to engage with receptacles (not illustrated) on the anchor 100. In this embodiment, the jaws 21, 22 apply a gripping force that is substantially perpendicular to the plane of the vertebral rod 110.

As illustrated in FIGS. 1 and 3, anchors 100 include a shaft 101 that is inserted into the vertebral member 120 and a head 102 that extends outward from the vertebral member 120. The head 102 may be fixedly positioned or movable relative to the shaft 101. The head 102 further includes a pair of spaced-apart arms 103 that form a channel 104 sized to receive the vertebral rod 110. The channel 104 includes an open side to allow insertion of the vertebral rod 110. In one embodiment, the open side is opposite from the shaft such that the anchor 100 is top-loading. A fastener 105 is configured to engage with the arms 103 to maintain the vertebral rod 110 in the channel 104. One type of anchor 100 is the CD-Horizon Legacy Fixed Angle Screw manufactured by Medtronic Sofamor Danek of Memphis, Tenn.

The reduction member 30 is pivotally attached to the gripper 20 and is configured to reduce the vertebral rod 110 into the anchor 100. As illustrated in FIGS. 1 and 2, the reduction member 30 includes a handle 31 and a shaft 32. The handle 31 is pivotally attached to the second jaw 22. The handle 31 may be attached to a proximal section of the second jaw 22 between the pivot 23 and the proximal end 25. Handle 31 includes a first end 33 attached to the second jaw 22 and an opposite second end 34. Handle 31 may also include a superior side 35 and opposing lateral sides 36. A pin, rivet, or the like 37 may extend through the lateral sides 36 and the second jaw 22 to pivotally connect the handle 31. An aperture 38 may extend through the superior side 35 of the handle 31 to receive the shaft 32.

The shaft 32 includes a distal end 40 configured to receive the vertebral rod 110, and an opposite proximal end 41. Threads 42 may extend along the entirety or a limited length of the shaft 32. The distal end 40 may include a receiver 43 formed by opposing arms 44. The receiver 43 is sized to receive the vertebral rod 110, and may include a shape that corresponds to the cross-sectional shape of the rod 110. The receiver 43 may include an open side that is positioned away from the shaft 32 to facilitate positioning the vertebral rod 110 into the channel 104 of the anchor 100. The receiver 43 and arms 44 may be formed by the shaft 32 itself, or may be a separate piece that is attached to the distal end 40 of the shaft 32. The proximal end 41 may include a polygonal shape or other like-feature to mate with a driving tool to provide a rotational force to the shaft 32.

The aperture 38 in the handle 31 may be threaded to engage with the threads 42 that extend along the shaft 32. Movement of the shaft 32 relative to the handle 31 is accomplished by rotation of the shaft 32. In another embodiment, aperture 38 includes an enlarged size that is greater than a cross-sectional size of the shaft 32. A plate is pivotally attached to the handle 31 and includes a threaded aperture to receive the shaft 32. The shaft 32 may be moved within the aperture 38 by pivoting the plate. In one specific embodiment, the plate is attached to the handle 31 between the opposing lateral sides 36.

The reduction member 30 is configured for coarse and fine movement of the shaft 32 during reduction of the vertebral rod 110. Coarse reduction includes pivoting the handle 31 relative to the gripper 20. This pivoting movement moves the shaft 32 and attached vertebral rod 110. Fine reduction includes rotating the shaft 32 and axially moving the shaft 32 by the threads relative to the handle 31. During use, coarse reduction may occur for initially moving the vertebral rod 110 a distance from the proximal section 57 of the capturing space 61. Fine reduction may then be used for the remaining movement that positions the vertebral rod 110 into the channel 104 of the anchor 100.

A locking member 50 may be attached to the gripper 20 to maintain attachment of the distal ends 24 to the anchor 100. The locking member 50 includes a head 51 and a shaft 52 that extends through one of the jaws 21, 22. The locking member 50 may be attached to the opposite jaw from the reduction member 30 for spacing reasons. The locking member 50 is attached to the gripper 20 on an opposite side of the pivot 23 from the distal ends 24 and in proximity to the proximal ends 25. The end of the shaft 52 contacts against the opposing jaw 21, 22. This contact causes the proximal ends 25 of the jaws 21, 22 to move apart which in turn causes the distal ends 24 to move together and lock onto the anchor 110. Locking member 50 may also include a wedged member, ratchet, or sliding sleeve.

A biasing member 54 may be positioned between the proximal ends 25. The biasing member 54 provides a force to separate the proximal ends 25 and thus move the distal ends 24 together. The biasing member 54 may include a coil spring that extends around the shaft 52 of the locking member 50. The coil spring includes a first end that contacts the first jaw 21, and a second end that contacts the second jaw 22. In one embodiment, the biasing member 54 and locking member 50 work in combination to maintain the gripper 20 attached to the anchor 110 in a default arrangement.

The locking member 50 and/or the biasing member 54 may also contact against the first end 33 of the handle 31. This contact causes the handle 31 to extend outward from the jaw 21, 22 to which it is connected.

The gripper 20 may also be formed as a single piece that does not include separate jaws 21, 22. FIGS. 7-10 includes the jaws 21, 22 being a single, unitary body. The jaws 21, 22 include an asymmetrical shape with the second jaw 22 including a curved shape and the first jaw 21 being substantially straight. The capture area 61 also includes a funnel shape with a wide proximal width that narrows to a small distal width at the distal ends 24.

The second jaw 22 includes a distal end 24a with opposing fingers 77 that are spaced apart to receive the anchor 100. The fingers 77 are positioned on the lateral sides of the distal ends 24a, 24b. The first jaw 21 includes a distal end 24b with a single finger 77.

Figure 7:
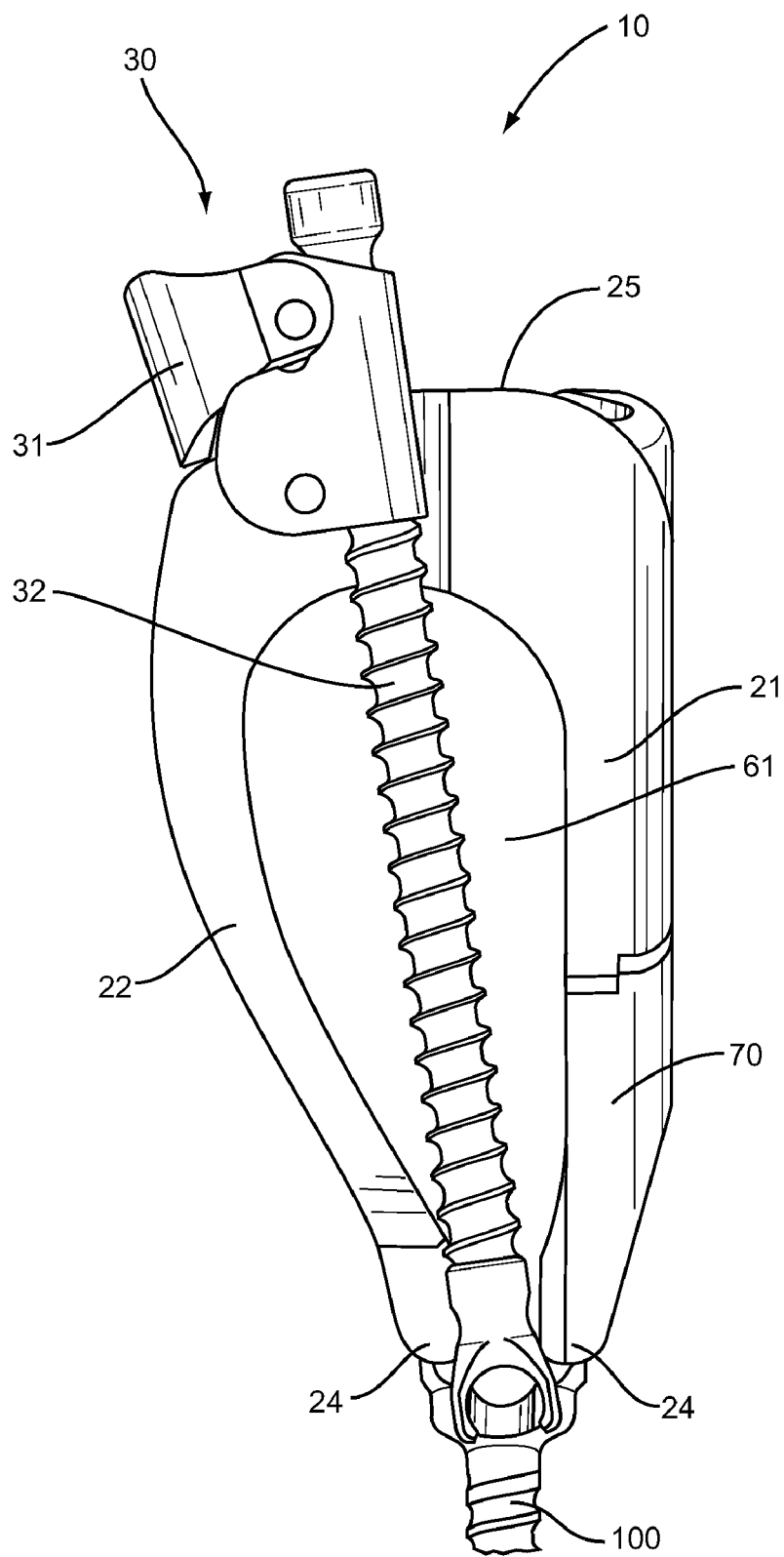
FIG. 7 is a side view of a reduction instrument according to one embodiment.
Figure 8:
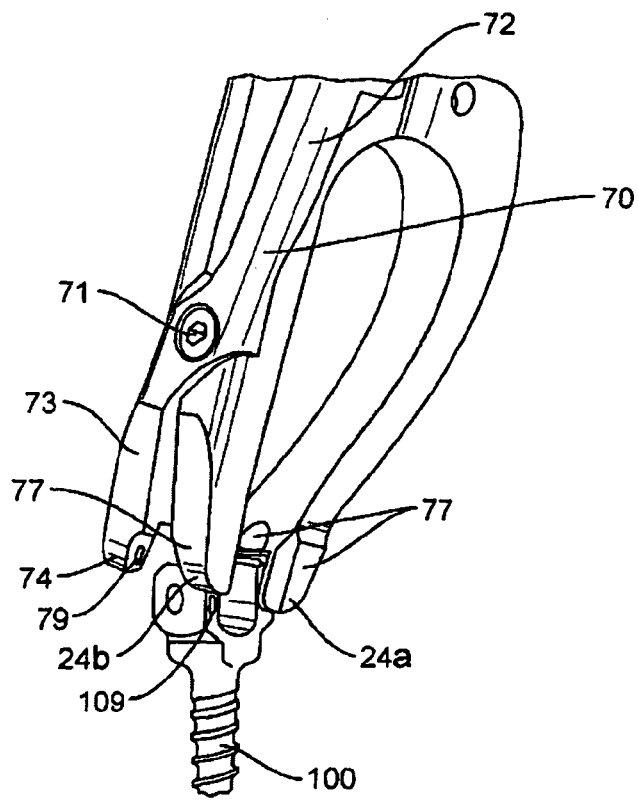
FIG. 8 is a partial perspective view of a gripper with a locking arm in an unlocked orientation according to one embodiment.

A locking arm 70 is pivotally connected to one of the jaws 21, 22. The locking arm 70 may be connected to the first jaw 21 as illustrated in FIG. 7 because of the straighter shape of the jaw 21 reduces the overall size of the locking arm 70. The locking arm 70 is connected to the gripper 20 with a pivot 71 such as a pin, rivet, or other like mechanical structure. A first section 72 is positioned on a proximal side of the pivot 71 and a second section 73 is positioned on a distal side. The second section 73 includes a distal end 74 that aligns with the distal end 24 of the jaw 21 when the locking arm 70 is in the locked orientation. The distal ends 24b and 74 form an opposing finger for the jaw 22 when the locking arm 70 is in the locked orientation. A lip 79 may extend outward from an inner edge of the distal end 74 as illustrated in FIG. 8. The lip 79 is inserted into a lateral recess 109 on the anchor arms 103. The first section 72 may include a contact surface 76 with a flat surface area for contact by the surgeon. The jaw 21 may also include recessed sections to receive the first and second sections 72, 73 when the arm 70 is in the locked orientation.

Figure 9:
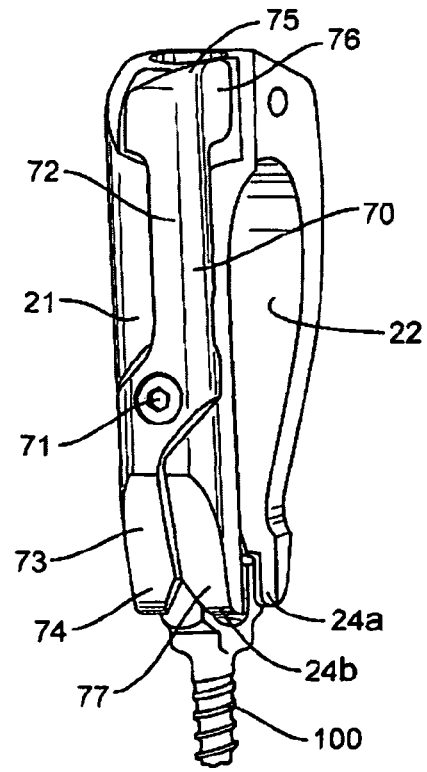
FIG. 9 is a perspective view of a gripper with a locking arm in a locked orientation according to one embodiment.

The locking arm 70 locks the instrument 10 to the anchor 100. The locking arm 70 is movable between a locked orientation that substantially overlaps the jaw 21, and an unlocked orientation with the distal and proximal ends 74, 75 away from the jaw 21. Attachment of the gripper 20 requires the locking arm 70 to initially be in an unlocked orientation as illustrated in FIG. 8. Initially, the distal end 24a of the second jaw 22 is placed on a first side of the anchor 100 with the fingers 77 positioned on opposing lateral sides. The distal end 24b of the first jaw 21 is positioned away from the anchor 100. The gripper 20 is then pivoted about the distal end 24a to position the single finger 77 of the distal end 24b against the anchor 100. As illustrated in FIG. 9, the locking arm 70 is then moved about pivot 71 with the distal end 74 moved against the anchor 100 opposite from the finger 77 on the distal end 24b. Further, the lip 79 may be inserted into the lateral recess 109 in the arm 103. The pivoting movement of the locking arm 70 may be performed by the surgeon applying a force to the contact surface 76 at the proximal end 75 to move the locking arm 70 about the pivot 71.

The locking arm 70 applies a locking force to the anchor 100 that is substantially parallel to the rod 110. This is different than one of the other embodiments with the pivoting jaws 21, 22 that apply a force substantially perpendicular to the rod 110.

The locking arm 70 may be secured in the locked orientation to maintain the attachment with the anchor 100. Various locking devices may be used to maintain the orientation, including a mechanical fastener that extends through the arm 70 and into the gripper 20, a clip that fits over the arm 70 and gripper 20, and the like.

Figure 10:
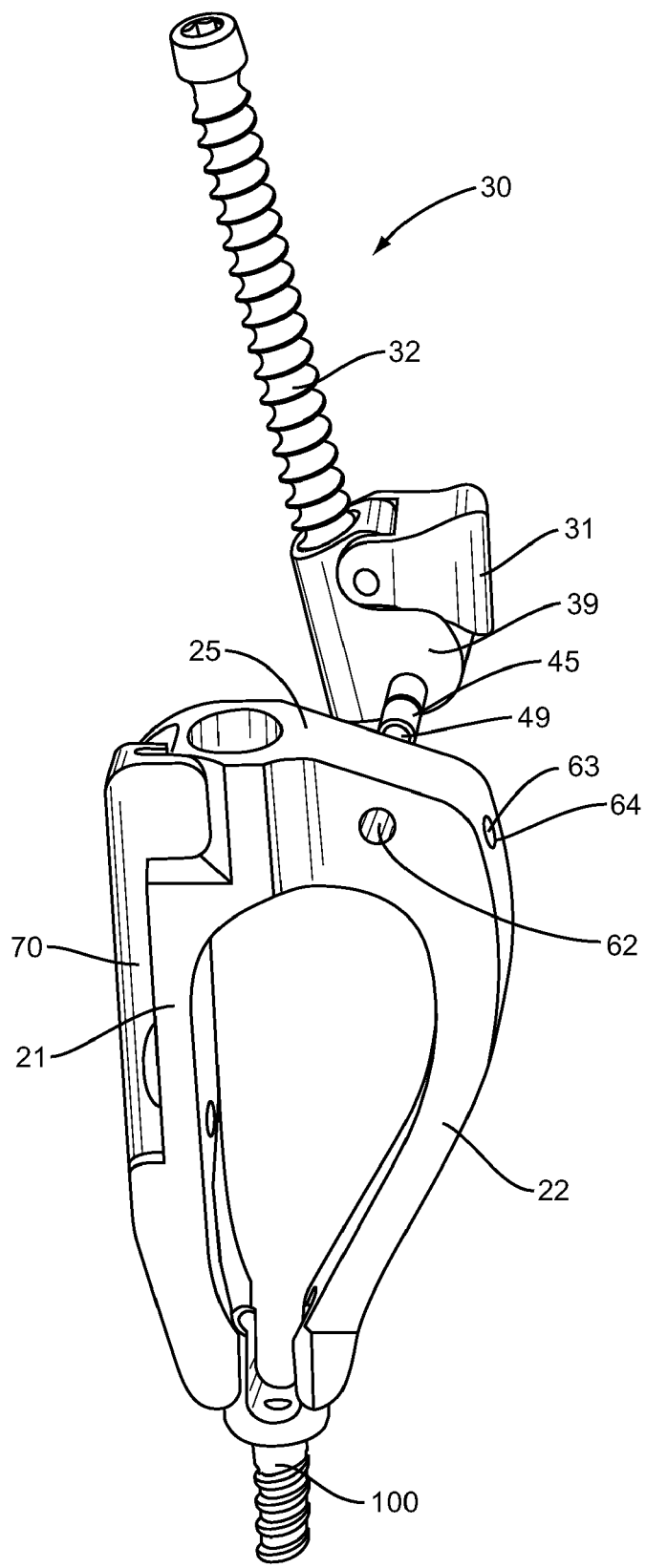
FIG. 10 is an exploded perspective view of a reduction instrument according to one embodiment.

A reduction member 30 that includes a body 39, handle 31 and shaft 32 is attached to a side of the gripper 20. FIG. 10 includes an exploded view of the reduction member 30 removed from the gripper 20. An extension 45 extends outward from the body 39 and fits within an aperture 62 in the gripper 20. A groove 49 may extend around the circumference of the extension 45. A ball plunger 63 may be inserted into a second aperture 64 in the gripper 20. The second aperture 64 is in communication with the aperture 62. A retractable ball tip at the end of the ball plunger 63 may seat within the groove 49 in the extension 45 to maintain the body 39 pivotally attached to the gripper 20. The extension 45 may also be attached by other methods including being threaded into the gripper 20 and adhesives. The body 39 is movable about an axis that extends through the extension 45 to adjust the position of the shaft 32 to accommodate a vertebral 110 at various positions within the capture space 61.

Figure 12:
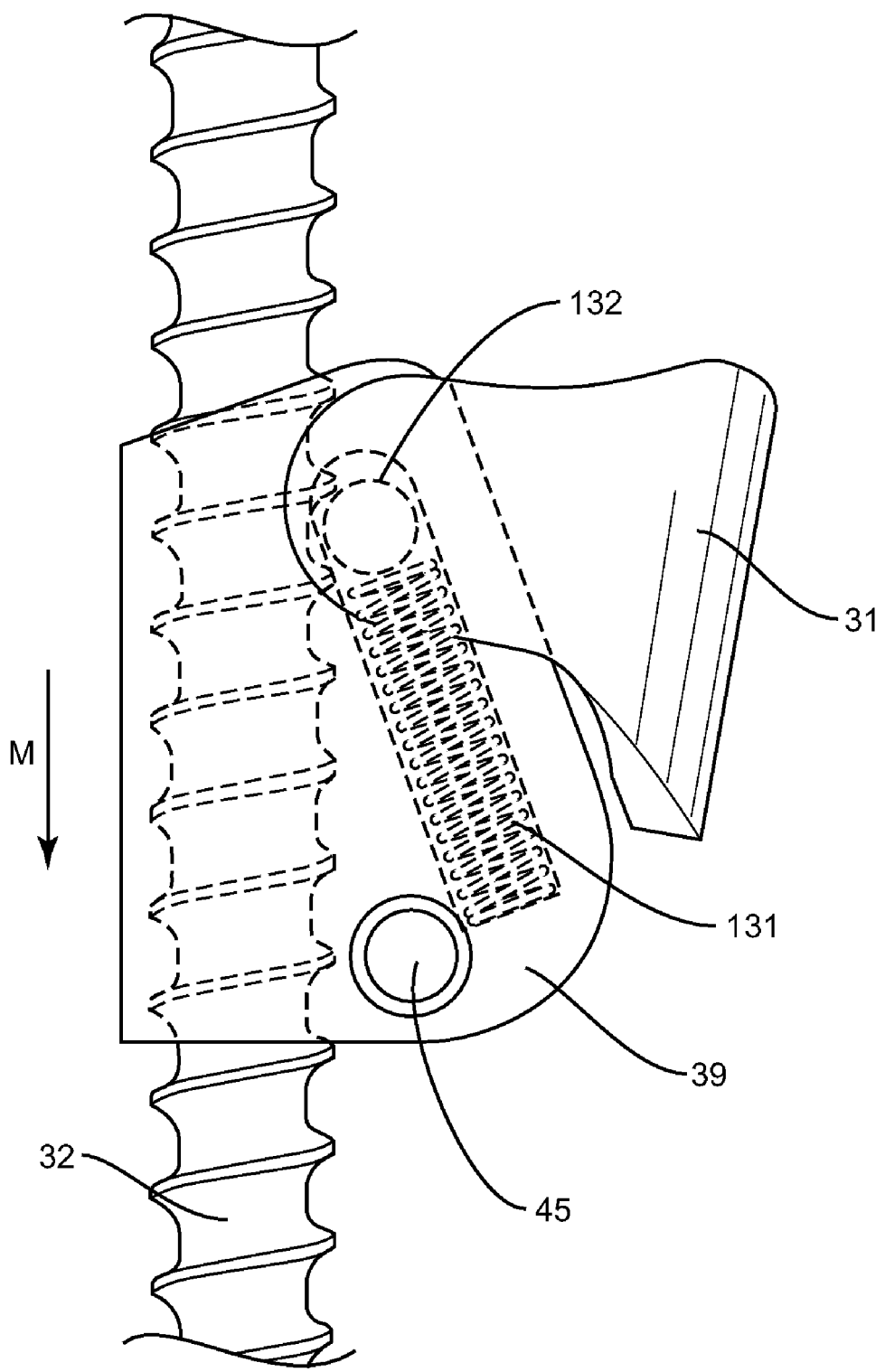
FIG. 12 is a schematic view of a quick-thread feature according to one embodiment.

The reduction member 30 may also include a quick-thread feature as illustrated in FIG. 12. A biasing member 131 is positioned in the body 39 to bias an obstruction member 132 against the shaft 32. The obstruction member 132 is also operatively connected to the handle 31. The obstruction member 132 may abut against the shaft 32 to allow the shaft 32 to move through the handle 31 through rotation. In another embodiment, the shaft 32 may include teeth and the obstruction member 132 acts as a ratchet mechanism to allow the shaft 32 to move in the direction of arrow M, and prevent movement in an opposite direction. In these embodiments, the handle 31 may be pivoted to move the obstruction member 132 away from the shaft 32 and allow for movement of the shaft 32 in the opposite direction.

Methods of using the instrument 10 initially require the anchors 110 be attached to the vertebral members along the section of the spine that is being treated. Anchors 110 may be attached to each of the vertebral members 120 along the treated section of the spine, or along a select few of the vertebral members 120.

An instrument 10 is then attached to each anchor 110. The attachment positions the distal ends 24 of the gripper 20 onto the anchor 110, and specifically onto the anchor arms 103. For the instrument disclosed in FIGS. 1-5, attachment of the instrument 10 includes pressing the proximal ends 25 of the jaws 21, 22 together and separating the distal ends 24. This may be performed by the surgeon squeezing the proximal ends 25 together. The distal ends 24 are then placed over the anchor 110 and the surgeon removes the force on the proximal ends 25 causing the distal ends 24 to contact against the arms of the anchor 100. The jaws 21, 22 are positioned with the channel 104 between the arms 103 facing into the capturing space 61. In the instrument of FIGS. 6-9, the locking arm 70 is moved to the unlocked orientation and the second jaw 22 is attached to one of the anchor arms 103. The gripper 20 is pivoted about the second jaw 22 to move the first jaw 21 into contact with the opposing anchor arm 103. Afterwards, the locking arm 70 is moved to the locked position to bring the distal end 74 against the anchor arm 103 to work in combination with the distal end 24b of the first jaw 21 and lock the gripper 20 to the anchor 100. Again, the channel 104 is positioned between the first and second jaws 21, 22 and facing into the capturing space 61. The attachment may also include the exterior of the anchor head 102 positioned against the scallops 27. Further, the tabs 26 that extend outward from the jaws 21, 22 may be positioned within receptacles in the exterior of the anchor head 102.

Once an instrument 10 is attached to each anchor 100, the vertebral rod 110 is inserted into the patient. The vertebral rod 110 is inserted into the patient in a top-to-bottom direction or a bottom-to-top direction. The leading end of the vertebral rod 110 is inserted into the patient and then threaded along the spine and through the capturing space 61 on each of the instruments 10. The enlarged size of the capturing space 61 facilitates this process. One example of an insertion device is disclosed in U.S. patent application Ser. No. 11/739,919 herein incorporated by reference.

The vertebral rod 110 may be formed of a biocompatible material, such as, for example, stainless steel or titanium. However, other materials are also contemplated, including, for example, titanium alloys, metallic alloys such as chrome-cobalt, polymer based materials such as PEEK, composite materials, or combinations thereof. The vertebral rod 110 may be substantially straight, or may be bent or contoured, either outside of the patient's body or in-situ, to more closely match the position, orientation and alignment of the vertebral members 120.

Once the vertebral rod 110 is positioned in the capturing space 61, the vertebral rod 110 is attached to the receiver 43 at the distal end of the shaft 32. The ability of the shaft 32 to move lateral and axially to cover the capturing space 61 facilitates the attachment.

After attachment, the vertebral rod 110 is moved axially downward along the gripper 20 and reduced into the anchor 100. The reduction member 30 is able to provide for course and fine reduction movement. The coarse movement includes pivoting the handle 31 relative to the gripper 20 and moving the vertebral rod 110 towards the anchor 100. Fine movement may include rotation of the shaft 32 relative to the handle 31 with the shaft 32 moving along the threads associated with the handle 31. In some embodiments, the coarse movement is originally performed to move the vertebral rod 110 from the proximal sections 57 of the capturing space 61. The fine movement is then performed to move the vertebral rod 110 through the remainder of the capturing space 61 and into the anchor channel 104.

Figure 11A:
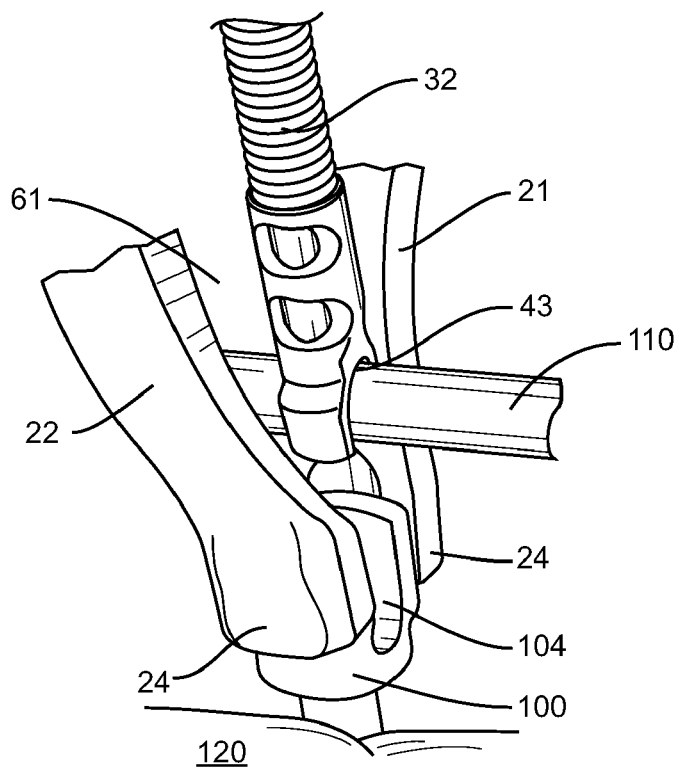
FIG. 11A is a perspective view of a vertebral rod attached to a shaft in proximity to an anchor according to one embodiment.
Figure 11B:
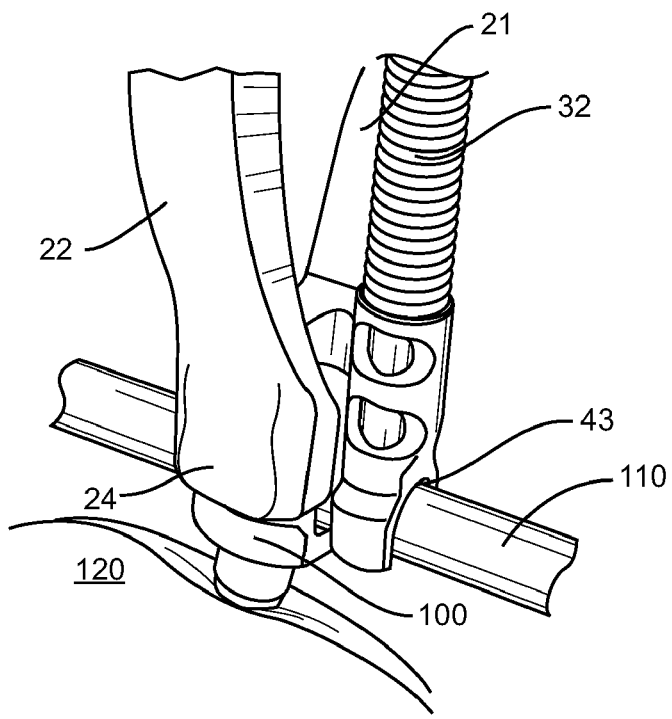
FIG. 11B is a perspective view of a vertebral rod attached to a shaft positioned in a channel of an anchor according to one embodiment.

FIGS. 11A and 11B illustrate the shaft 32 attached to the vertebral rod 110 as it is moved into the anchor 100. As illustrated in FIG. 11A, the receiver 43 is attached to the vertebral rod 110. The vertebral rod 110 is in the lower, distal section 59 of the capturing space 61. The reduction member 30 is actuated either through coarse or fine movement to continue movement of the vertebral rod 110 into the channel 104 as illustrated in FIG. 11B. The receiver 43 is positioned on a lateral side of the jaws 21, 22 to allow the vertebral rod 110 to be moved into the channel 104. This positioning prevents the receiver 43 from contacting the jaws 21, 22 and preventing the vertebral rod 110 from being fully seated into the channel 104.

While the vertebral rod 110 is in the channel 104, the fastener 105 is inserted and attached to the arms 103 to prevent escape. In one embodiment, the fastener 105 is threaded onto the arms 103. Because the receiver 43 is on the lateral side of the jaws 21, 22 and the anchor 100, the anchor 100 is accessible for attachment of the fastener 105.

The instrument 10 may be removed from the anchor 10 after the fastener 105 is attached to the anchor 100 and the vertebral rod 110 is secured in the channel 104. For the instrument 100 of FIGS. 1-5, detachment includes compressing the proximal ends 25 of the jaws 21, 22. This movement pivots the jaws 21, 22 thus distancing the distal ends 24 away from the anchor 100 to allow removal. For the instrument of FIGS. 7-10, the locking arm 70 is moved to the unlocked orientation and the gripper 20 is removed from the anchor 100. In both embodiments, the receiver 43 is configured to be detached from the vertebral rod 110 after being secured in the channel 104. The receiver 43 may include an opening that faces away from the shaft 32. Detachment occurs as the shaft 32 is axially moved upward along the gripper and the vertebral rod 110 escapes through the opening as it is held in the channel 104.

In the embodiments described above, the instrument 10 is attached to the anchor 100 prior to insertion of the vertebral rod 110. The instrument 10 may also be attached to the anchor 100 after the vertebral rod 110 is inserted into the patient. The instrument 10 is inserted into the patient with the vertebral rod 110 passing through the space between the jaws 21, 22. In this manner, the instrument 10 moves and thereby positions the vertebral rod 110 into the capturing space 61.

The gripper 20 may include various structures to disconnect from the anchor 100. The gripper 20 may include jaws 21, 22 that pivot apart. The jaws 21, 22 may also be configured for parallel sliding onto and off of the anchor 100. One or both jaws 21, 22 may also be made from multiple sections that are movable relative to one another. One or both jaws 21, 22 may also be constructed entirely or partially from a flexible material that is elastic enough to bend during attachment and removal from the anchor 100.

In another embodiment, the gripper 20 may be made from a single piece. The jaws 21, 22 may be manually opened by applying a compressive force to the proximal ends 25. When the force is removed, the jaws 21, 22 move back towards each other allowing attachment to the anchor 100. A wedge or other like locking member may be connected to the proximal ends to maintain the jaws 21, 22 attached to the anchor 100.

Figure 13:
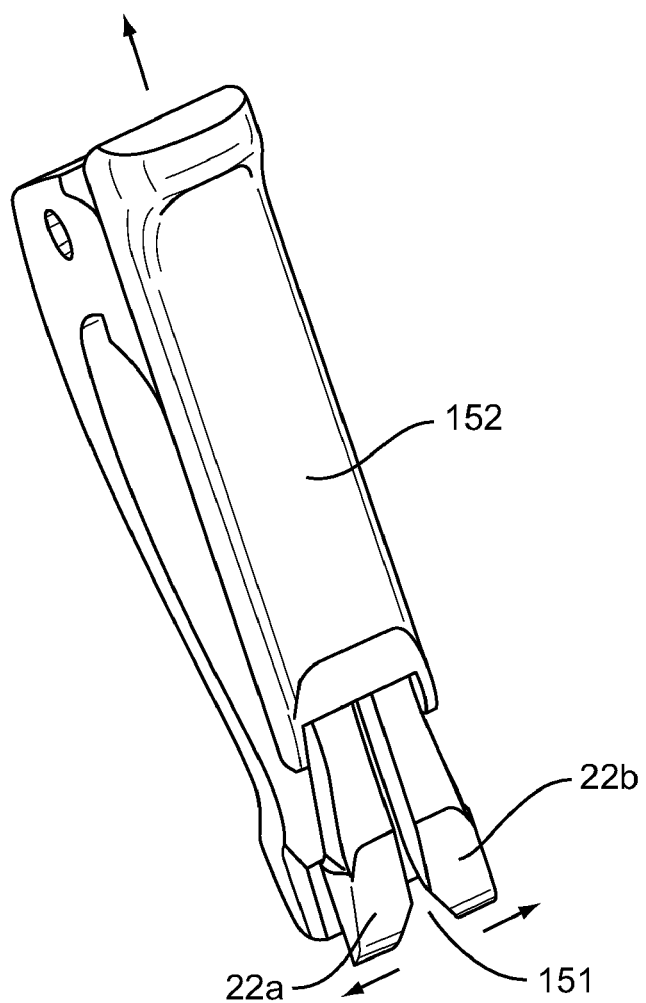
FIG. 13 is a perspective view of a gripper with an attachment mechanism according to one embodiment.

FIG. 13 includes an embodiment with jaw 22 including a first section 22a and a second section 22b separated by a gap 151. A sleeve 152 is attached to the jaw 22 and may slide along the length. When the sleeve 152 is slid away from the ends of the sections 22a, 22b as illustrated in FIG. 13, the sections 22a, 22b move apart and allow for the jaw 22 to be attached to the anchor 100. When the sleeve 152 is slid downward towards the ends, the sections 22a, 22b move together and attach to the anchor 100. This movement of the sections 22a, 22b may be caused by the jaw 22 being constructed from a flexible material and/or a biasing member (not illustrated) positioned within the gap 151 that biases the sections 22a, 22b apart. One or both of jaws 21, 22 may include this two-section construction.

The anchors 100 may include a threaded shaft that is inserted into an aperture in the vertebral member 120. The anchors 100 may also include spinal hooks configured for engagement about a portion of a vertebral member 120, bolts, pins, nails, clamps, staples and/or other types of bone anchor devices capable of being anchored in or to vertebral member 120.

The anchors 100 may be fixed-angle anchors with the head 102 fixedly positioned relative to the shaft 101. Fixed-angle anchors may be used in regions of the spine exhibiting relatively high intervertebral angles. The anchors 100 may also be multi-axial and allow the head 102 to be selectively pivoted or rotated relative to the shaft 101 along multiple planes or about multiple axes. In one such embodiment, the head 102 includes a receptacle for receiving a spherical-shaped portion of a threaded shaft 101 therein to allow the head 102 to pivot or rotate relative to the shaft 101. A locking member or crown may be compressed against the spherical-shaped portion via a fastener to lock the head 102 at a select angular orientation relative to the shaft 101. The use of multi-axial anchors may be beneficial for use in the lower lumbar region of the spine, and particularly below the L4 vertebral member, where lordotic angles tend to be relatively high compared to other regions of the spinal column.

In one embodiment, the treatment of the deformity is performed percutaneously. In other embodiments, the treatment is performed with an open approach, semi-open approach, or a muscle-splitting approach.

The instrument 10 in the above embodiments includes the gripper 20 and reduction member 30. These elements may also be used individually without the other. In one embodiment, the gripper 20 is used without the reduction member 30.

Figure 14:
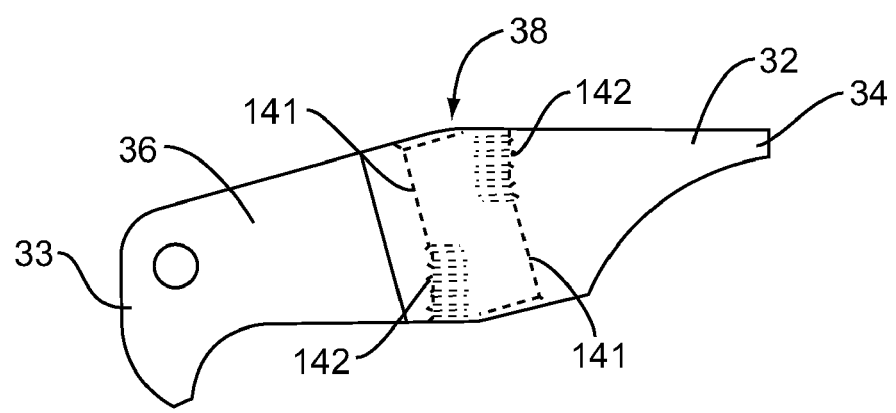
FIG. 14 is a schematic view of a handle with an aperture that facilitates various movement of a shaft relative to the handle according to one embodiment.

FIG. 14 includes a handle 31 that provides for two distinct movement mechanisms for the shaft 32. The aperture 38 extends through the handle 31 and includes opposing smooth sections 141 and opposing threaded sections 142. The opposing sections are on opposite sides and levels of the aperture 38. As viewed in FIG. 14, the smooth sections 141 are on the upper-left and lower-right sections of the aperture 38. The threaded sections 142 are on the upper-right and lower-left sections of the aperture 38. When the handle 31 is pivoted to a disengaged orientation, the shaft 32 (not illustrated in FIG. 14) contacts against the non-threaded sections 141 which allows for the shaft 32 to freely slide through the handle 31. When the handle 31 is pivoted to an engaged orientation, the shaft 32 contacts against the threaded sections 142 and threadingly engages the threads on the shaft 32.

One method of using the instrument 10 includes inserting the assembled instrument into the patient and attaching the gripper 20 to the anchor 100. Another method includes separately inserting the instrument 10 in a disassembled condition. This may include the first and second jaws 21, 22 being separate when inserted into the patient. Once inserted, the jaws 21, 22 are connected together and the instrument 10 is attached to the anchor 100 and used as described above. The connecting of the jaws 21, 22 while in the patient may include inserting the pivot 23 through receiving apertures in each of the jaws 21, 22. The reduction member 30 may be attached to one of the jaws 21, 22 at the time of insertion into the patient, or may be attached after insertion of the jaws 21, 22.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An instrument for moving a vertebral rod into an anchor attached to a vertebral member, the instrument comprising:
   a gripper including opposing first and second jaws each with a distal end to attach to the anchor and a proximal end, wherein the first jaw is substantially straight and the second jaw is bowed in a first plane away from the first jaw, and wherein an intermediate section of the second jaw is bowed outward away from a second plane that extends through the proximal and distal ends of the first and second jaws, and wherein a proximal section of the second jaw is substantially straight;
   an asymmetrical capturing space formed between inner edges of the first and second jaws and the distal ends, the capturing space including a funnel shape with a first end having a first width and a second end having a second width, wherein the first end is towards the proximal ends of the first and second jaws and has a larger width than the second end that is at the distal ends of the first and second jaws;
   a handle pivotally attached to one of the first and second jaws between the proximal end of the one of the first and second jaws and the first end of the capturing space; and
   an elongated shaft attached to the handle and including a first end with a receiver with an opening facing away from the elongated shaft and configured to engage with the vertebral rod, the elongated shaft being movable relative to the handle and being movable relative to the gripper to position the receiver throughout lateral and axial locations of the capturing space to move the vertebral rod towards the distal ends of the first and second jaws and into the anchor.

2. The instrument of claim 1, wherein the first and second jaws are separate pieces that are pivotally connected together with the gripper configured to be movable between an unlocked orientation with a distance between the first and second jaw distal ends being greater than a width of the anchor and a locked orientation with the distance between the distal ends being substantially equal to a width of the anchor.

3. The instrument of claim 2, wherein each of the jaws includes a receiving aperture sized to receive a pivot pin to attach the jaws together, the receiving apertures being located to receive the pivot pin after the jaws have been inserted into a patient and prior to being attached to the anchor.

4. The instrument of claim 2, further comprising a locking member attached near the proximal end of the one of the first and second jaws, the locking member including a locking shaft that extends through the one of the first and second jaws jaw and includes a contact end that contacts an inner edge of the other of the first and second jaws to prevent further separation of the first and second jaw distal ends.

5. The instrument of claim 4, further comprising a biasing member positioned between the proximal ends of the first and second jaws and including a first end that contacts the first jaw and a second end that contacts the second jaw, the biasing member configured to apply a biasing force to the gripper to force the first and second jaw distal ends towards the locked orientation.

6. The instrument of claim 1, wherein the gripper includes an asymmetrical exterior shape to facilitate insertion to the vertebral member.

7. The instrument of claim 1, further comprising a locking arm that is pivotally attached to at least one of the first jaw and the second jaw and movable between an unlocked orientation with a distal end of the locking arm positionec away from the distal end of at least one of the first jaw and the second jaw and a locked orientation with the distal end of the locking arm positioned in proximity to the distal end of at least one of the first jaw and the second jaw.

8. An instrument for moving a vertebral rod into an anchor attached to a vertebral member comprising:
 a gripper comprising:
  a first jaw, and
  a second jaw that is bowed away from the first jaw, wherein an intermediate section of the second jaw is bowed outward away from a plane that extends through proximal and distal ends of the first and second jaws, and wherein a proximal section of the second jaw is substantially straight;
 a pivot positioned between the proximal and distal ends of the first and second jaws to pivotally attach the first and second jaws together;
 an asymmetrical capturing space formed between inner sides of the first and second jaws between the pivot and the first and second jaw distal ends, the capturing space configured to receive the vertebral rod and including a funnel shape that narrows from a first end near the pivot to a second end at the distal ends;
 a handle pivotally attached to one of the first and second jaws between the pivot and the proximal end of the one of the first and second jaws; and
 an elongated shaft movably attached to the handle and including a first end with a receiver configured to engage with the vertebral rod in the capturing space, wherein the handle is movable relative to the gripper to position the receiver throughout lateral and medial locations of the capturing space to move the vertebral rod towards the second end of the capturing space and into the anchor.

9. The instrument of claim 8, wherein the first jaw is substantially straight.

10. The instrument of claim 8, wherein a width of the capturing space continuously narrows between the first end of the capturing space and the second end of the capturing space.

11. The instrument of claim 8, wherein an outer width of the gripper measured between outer sides of the first and second jaws includes an asymmetrical shape that narrows towards the distal ends of the first and second jaws.

12. The instrument of claim 8, further comprising a locking member that includes a head and a locking shaft, the locking shaft extends through one of the first and second jaws between the pivot and the proximal end of the first and second jaws and includes a contact surface at an end of the shaft that contacts against an inner surface of the other of the first and second jaws to prevent the first and second jaw proximal ends from moving together.

13. The instrument of claim 8, wherein the first and second jaws include apertures sized to receive the pivot, the apertures and pivot being configured for attaching the first and second jaws together with the pivot after the first and second jaws are inserted in to a patient and prior to attachment to the anchor.

* * * * *

UNITED STATES PATENT AND TRADEMARK OFFICE
CERTIFICATE OF CORRECTION

PATENT NO.         : 8,246,623 B2
APPLICATION NO.    : 12/358416
DATED              : August 21, 2012
INVENTOR(S)        : Peultier et al.

It is certified that error appears in the above-identified patent and that said Letters Patent is hereby corrected as shown below:

In Column 11, Line 14, in Claim 4, delete "second iaw" and insert -- second jaw --, therefor.

In Column 11, Line 21, in Claim 5, delete "second iaw" and insert -- second jaw --, therefor.

In Column 11, Line 28, in Claim 7, delete "positionec" and insert -- positioned --, therefor.

Signed and Sealed this
Eighteenth Day of December, 2012

David J. Kappos
*Director of the United States Patent and Trademark Office*